US010376506B2

United States Patent
Morillo et al.

(10) Patent No.: US 10,376,506 B2
(45) Date of Patent: Aug. 13, 2019

(54) USE OF AN OPIOID RECEPTOR ANTAGONIST WITH KAPPA-ACTIVITY AND VORTIOXETINE FOR TREATMENT OF DEPRESSIVE DISORDER WITH MELANCHOLIC FEATURES

(71) Applicant: H. Lundbeck A/S, Valby (DK)

(72) Inventors: Connie Sanchez Morillo, West Milford, NJ (US); Gennady N. Smagin, Newark, DE (US)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 15/105,701

(22) PCT Filed: Dec. 18, 2014

(86) PCT No.: PCT/EP2014/078515
§ 371 (c)(1),
(2) Date: Jun. 17, 2016

(87) PCT Pub. No.: WO2015/091833
PCT Pub. Date: Jun. 25, 2015

(65) Prior Publication Data
US 2016/0310488 A1    Oct. 27, 2016

(30) Foreign Application Priority Data

Dec. 20, 2013  (DK) ................................ 2013 00710
Oct. 16, 2014  (DK) ................................ 2014 00590

(51) Int. Cl.
*A61K 31/4965*   (2006.01)
*A61K 31/44*     (2006.01)
(Continued)

(52) U.S. Cl.
CPC .......... *A61K 31/495* (2013.01); *A61K 31/485* (2013.01)

(58) Field of Classification Search
CPC ........................... A61K 31/485; A61K 31/496
(Continued)

(56) References Cited

U.S. PATENT DOCUMENTS 5,013,740 A      5/1991  Glover
2002/0091075 A1* 7/2002  Carlezon, Jr. ........ A61K 31/401
                                                      514/1
(Continued)

FOREIGN PATENT DOCUMENTS

EP       0451009       10/1991
WO       WO 2002/049643  6/2002
(Continued)

OTHER PUBLICATIONS

Sanchez, C. et al. (2014) "Vortioxentine, a Novel Antidepressant with Multimodal Activity: Review of Preclinical and Clinical Data," Pharmacol. Ther. 145:43-57.
(Continued)

*Primary Examiner* — Shengjun Wang
(74) *Attorney, Agent, or Firm* — Wilmer Cutler Pickering Hale and Dorr LLP (57) ABSTRACT

The present invention relates to an opioid antagonist with κ-activity for use in treatment of depressive disorder with melancholic features. The invention further relates to the combination of an opioid antagonist with κ-activity and vortioxetine for use in treatment of depressive disorder with melancholic features. The invention also relates to pharmaceutical compositions comprising an opioid antagonist with κ-activity and vortioxetine.

14 Claims, 2 Drawing Sheets

(51) Int. Cl.
A61K 31/495 (2006.01)
A61K 31/485 (2006.01)
(58) Field of Classification Search
USPC .......................................... 514/282, 255.03
See application file for complete search history.

(56) References Cited

U.S. PATENT DOCUMENTS

| | | | |
|---|---|---|---|
| 2003/0181475 A1 | 9/2003 | Kaiko et al. | |
| 2007/0259939 A1 | 11/2007 | Stebbing | |
| 2008/0045610 A1* | 2/2008 | Michalow | A61K 31/137 514/789 |
| 2011/0201617 A1* | 8/2011 | Moore | A61K 31/495 514/252.12 |
| 2016/0058754 A1 | 3/2016 | Meulien et al. | |

FOREIGN PATENT DOCUMENTS

| | | |
|---|---|---|
| WO | WO 2003/013524 | 2/2003 |
| WO | WO 2003/029232 | 4/2003 |
| WO | WO 2007/144005 | 12/2007 |
| WO | WO 2008/066916 | 6/2008 |
| WO | WO 2008/113359 | 9/2008 |
| WO | WO 2010/136039 | 12/2010 |
| WO | WO 2011/136376 | 3/2011 |
| WO | WO-2011/136376 A1 | 11/2011 |
| WO | WO 2012/059103 | 5/2012 |
| WO | WO 2014/120936 | 8/2014 |
| WO | WO 2014/170351 | 10/2014 |

OTHER PUBLICATIONS

"K-Opioid Receptor," Wikipedia (10 pages).
Adell, A. (2010) "Lu-AA21004, a Multimodal Serotonergic Agent, for the Potential Treatment of Depression and Anxiety," IDrugs 13(12):900-910.
Carlezon W.A. et al. (2009) "Kappa-Opioid Ligands in the Study and Treatment of Mood Disorders," Pharmacol. Ther. 123(3):334-343.
Harden, M.T. et al. (2012) "Antidepressive Effects of the K-Opioid Receptor Agonist Salvinorin A in a Rat Model of Anhedonia," Behav. Pharmacol. 23(7):710-715.
International Search Report PCT/EP2014/078515 (WO 2015/091833) (dated 2015) (5 pages).
Karhuvaara, S. et al., (2007) "Targeted Nalmefene with Simple Medical Management in the Treatment of Heavy Drinkers: A Randomized Double-Blind Placebo-Controlled Multicenter Study," Alcohol Clin. Exp. Res. 31(7):1179-1187.
Salloum, I.M. et al. (1998) "Naltrexone Utility in Depressed Alcoholics," Psychopharmacol. Bull. 34(1):111-115 (Abstract Only).
Written Opinion of the International Searching Authority PCT/EP2014/078515 (WO 2015/091833) (dated 2015) (8 pages).
Alvarez, E., et al. (2012) "A Double-Blind, Randomized, Placebo-Controlled, Active Reference Study of Lu AA21004 in Patients with Major Depressive Disorder," Int'l J. Neuropsychopharmacol. 15:589-600.
Bang-Andersen, B., et al. (2011) "Discovery of 1-[2-(2,4-Dimethylphenylsulfanyl)phenyl]piperazine (Lu AA21004): A Novel Multimodal Compound for the Treatment of Major Depressive Disorder," J. Med. Chem. 54:3206-3221.
Blanco, C., et al. (2012) "Differences Among Major Depressive Disorder with and without Co-Occurring Substance Use Disorders and Substance-Induced Depressive Disorder: Results from the National Epidemiologic Survey on Alcohol and Related Conditions," J. Clin. Psychiatry 73:865-873.
Carlezon Jr., W.A., et al. (2007) "Intracranial Self-Stimulation (ICSS) in Rodents to Study the Neurobiology of Motivation," Nat. Protoc. 2(11):2987-2995.

Carr, G.V., et al. (2010) "Antidepressant-Like Effects of κ-Opioid Receptor Antagonists in Wistar Kyoto Rats," Neuropsychopharmacol. 35:752-763.
Dragheim, M., et al. (2011) "A Double-Blind, Randomised, Placebo-Controlled, Relapse-Prevention Study with Lu AA21004 in Patients with Major Depressive Disorder," Eur. Neuropsychopharmacol. 21(suppl 3): S396-S397.
Grant, B.F., et al. (1995) "Comorbidity Between DSM-IV Alcohol Use Disorders and Major Depression: Results of a National Survey," Drug and Alcohol Dependence 39:197-206.
Gual, A., et al. (2012) "A Randomised, Double-Blind, Placebo-Controlled, Efficacy Study of Nalmefene, As-Needed Use, in Patients with Alcohol Dependence," Eur. Neuropsychopharmacol. 23:1432-1442.
Harden, M.T., et al. (2012) "Antidepressive Effects of the κ-Opioid Receptor Agonist Salvinorin A in a Rat Model of Anhedonia," Behavioural Pharmacol. 23(7)710-715.
Hodos, W. (1961) "Progressive Ratio as a Measure of Reward Strength," Science 134(3483):943-944.
Katona, C., et al. (2012) "A Randomized, Double-Blind, Placebo-Controlled, Duloxentine-Referenced, Fixed-Dose Study Comparing the Efficacy and Safety of Lu AA21004 in Elderly Patients with Major Depressive Disorder," Int'l Clinical Psychopharmacol. 27:215-223.
Kessler, R.C., et al. (1997) "Lifetime Co-Occurrence of DSM-III-R Alcohol Abuse and Dependence with Other Psychiatric Disorders in the National Comorbidity Survey," Arch. Gen. Psychiatry 54:313-321.
Knoll, A.T., et al. (2010) "Dynorphin, Stress, and Depression," Brain Res. 1314:56-73.
Land, B.B., et al. (2009) "Activation of the Kappa Opioid Receptor in the Dorsal Raphe Nucleus Mediates the Aversive Effects of Stress and Reinstates Drug Seeking," PNAS 106(45):19168-19173.
Mague, S.D., et al. (2003) "Antidepressant-Like Effects of κ-Opioid Receptor Antagonists in the Forced Swim Test in Rats," J. Pharmacol. Exp. Thera. 305:323-330.
Mann, K., et al. (2013) "Extending the Treatment Options in Alcohol Dependence: A Randomized Controlled Study of As-Needed Nalmefene," Biol. Psychiatry 73:706-713.
Markou, A., et al., (1993) "Animal Models of Drug Craving," Psychopharmacol. 112:163-182.
Mason, B.J., et al. (1999) "A Double-Blind, Placebo-Controlled Study of Oral Nalmefene for Alcohol Dependence," Arch. Gen. Psychiatry 56:719-724.
Moore, N., et al. (2008) "Lu AA21004: A Novel Potential Treatment for Mood Disorders," Eur. Neuropsychopharmacol. 18(supple 4):S321.
Mørk, A., et al. (2011) "Lu AA21004, A Novel Antidepressant, Modulates Neurotransmitter Levels and Theta Oscillations, and Exerts Pro-Cognitive Effects in Rats," Eur. Neuropsychopharmacol. 21(suppl 4): S407-S408.
Nielsen, C.K., et al. (2000) "Intracranial Self-Stimulation and Sucrose Intake Differ as Hedonic Measures Following Chronic Mild Stress: Interstrain and Interindividual Differences," Behavioural Brain Res. 107:21-33.
Pfeiffer, A., et al. (1986) "Psychotomimesis Mediated by κ Opiate Receptors," Science 233(4765):774-776.
Sher, L., et al. (2008) "Depressed Patients with Co-Occurring Alcohol Use Disorders: A Unique Patient Population," J. Clin. Psychiatry 69:907-915.
Swendsen, J.D., et al. (1998) "The Comorbidity of Alcoholism with Anxiety and Depressive Disorders in Four Geographic Communities," Comprehensive Psychiatry 39(4):176-184.
Swendsen, J.D., et al. (2000) "The Comorbidity of Depression and Substance Use Disorders," Gin. Psychol. Rev. 20(2):173-189.
Thase, M.E., et al. (2001) "Comorbid Alcoholism and Depression: Treatment Issues," J. Clin. Psychiatry 62(suppl 20):32-41.
Todtenkopf, M.S., et al. (2004) "Effects of κ-Opioid Receptor Ligands on Intracranial Self-Stimulation in Rats," Psychopharmacol. 172:463-470.
Walker, B.M., et al. (2008) "Pharmacological Evidence for a Motivational Role of κ-Opioid Systems in Ethanol Dependence," Neuropsychopharmacol. 33:643-652.

(56) References Cited

OTHER PUBLICATIONS

Westrich, L., et al. (2012) "In vitro and in vivo Effects of the Multimodal Antidepressant Vortioxetine (Lu AA21004) at Human and Rat Targets," Abstracts, Int'l J. Psychiatry Clin. Pract. 15(suppl 1):47.

Singapore Search Report and Written Opinion SG 11201604944P (2017) (9 pages).

International Search Report and Written Opinion issued in International Patent Application No. PCT/DK2008/050063 dated Sep. 19, 2008 by European Patent Office as International Searching Authority (16 pages total).

Halverson et al., "Depression With Melancholic Features," Medscape, Depression Clinical Presentation: History, Physical Examination, Major Depressive Disorder (1 page), retrieved from https://emedicine.medscape.com/article/286759-clinical#b6 (last retrieved on Mar. 21, 2019).

\* cited by examiner

USE OF AN OPIOID RECEPTOR ANTAGONIST WITH KAPPA-ACTIVITY AND VORTIOXETINE FOR TREATMENT OF DEPRESSIVE DISORDER WITH MELANCHOLIC FEATURES

This application is a U.S. National Phase Entry under 35 U.S.C. § 371 of International Application No. PCT/EP 2014/078515, filed Dec. 18, 2014, which claims priority to DK Application No. PA201400590, filed Oct. 16, 2014, and DK Application No. PA201300710, filed Dec. 20, 2013.

FIELD OF THE INVENTION

The present invention relates to an opioid antagonist with κ-activity for use in treatment of depressive disorder with melancholic features. The invention further relates to the combination of an opioid antagonist with κ-activity and vortioxetine for use in treatment of depressive disorder with melancholic features. The invention also relates to pharmaceutical compositions comprising an opioid antagonist with κ-activity and vortioxetine.

BACKGROUND OF THE INVENTION

An opioid antagonist is a receptor antagonist that acts on opioid receptors. Naloxone and naltrexone are commonly used opioid antagonists which are competitive antagonists that do not activate the receptors. This effectively blocks the receptor, preventing the body from responding to opiates and endorphins.

Some opioid antagonists are not pure antagonists but in fact do produce some weak opioid partial agonist effects, and can produce analgesic effects when administered in high doses to opioid-naive individuals. Examples of such compounds include nalorphine and levallorphan.

The weak partial agonist effect can be useful for some purposes, and has previously been used for purposes such as long-term maintenance of former opioid addicts using nalorphine, however it can also have disadvantages such as worsening respiratory depression in patients who have overdosed on non-opioid sedatives such as alcohol or barbiturates. Naloxone on the other hand has no partial agonist effects, and is in fact a partial inverse agonist at μ opioid receptors, and so is the preferred antidote drug for treating opioid overdose.

Naltrexone is also a partial inverse agonist, and this property is exploited in treatment of opioid addiction, as a sustained course of low-dose naltrexone can reverse the altered homeostasis which results from long-term abuse of opioid agonist drugs.

Buprenorphine is an opioid with both partial agonist and antagonist actions. Nor-binaltorphimine (nor-BNI) is a selective κ-opioid receptor antagonist.

Nalmefene [17-(cyclopropylmethyl)-4,5-alpha-epoxy-6-methylenemorphinan-3,14-diol], an example of an opioid antagonist, has the following general molecular formula:

and can be prepared using methods that are well known in the art e.g. from manufacturing naltrexone from noroxymorphone as described in WO 2012/059103 and subsequently manufacturing nalmefene from naltrexone e.g. by the Wittig reaction as described in WO 2010/136039. Nalmefene hydrochloride dihydrate is disclosed in WO 2010/136039.

Nalmefene is an opioid system modulator with a distinct μ, δ, and κ receptor profile. In vitro studies have demonstrated that nalmefene is a selective opioid receptor ligand with antagonist activity at the μ and δ receptors and partial agonist activity at the κ receptor.

The major feature of nalmefene is it's activity on K-opioid receptors with $Ki/EC_{50}$ of 1.6 nM. On μ-opioid receptors and δ-opioid receptors the activities are ($Ki/EC_{50}$ of 1.8 nM) and ($Ki/EC_{50}$ of 40 nM), respectively. The understanding of the role of the kappa opioid system in mediating mood has grown substantially in the last decade. Kappa-selective opioid agonists, including U-69593 and U-50488, produce anhedonia and a prodepressive phenotype in rodent models, including intracranial self-stimulation and forced swim test. In humans, kappa agonist administration (e.g., MR 2034 or salvinorin A) produces robust dissociative effects and cognitive disruption that partially, but not completely, overlap with symptoms associated with classic serotonergic hallucinogens. Moreover, the prodepressive phenotype produced by stress or kappa receptor activation in rodents is blocked by kappa antagonists or by genetic deletion of dynorphin or the kappa opioid receptor.

The efficacy and tolerability of nalmefene in the treatment of alcohol dependence have been evaluated in three phase III studies (two confirmatory 6-month efficacy studies and one 1-year safety study) conducted by Lundbeck (Mann et al. Extending the Treatment Options in Alcohol Dependence: A Randomized Controlled Study of As-Needed Nalmefene. *Biol. Psychiatry*. (2013) 73 (8): 706-713); Gual et al. A randomised, double-blind, placebo-controlled, efficacy study of nalmefene, as-needed use, in patients with alcohol dependence. *Eur. Neuropsychopharmacol*. (2013) 11: 1432-1442); and five studies in alcohol use disorders conducted by the company Biotie (Karhuvaara et al. *Alcohol. Clin Exp Res*. (2007) 31: 1179-1187).

A marketing authorisation was granted in the European Union (EU) in February 2013 for oral nalmefene (tradename Selincro®) for the reduction of alcohol consumption in adult patients with alcohol dependence who have a high drinking risk level (DRL), without physical withdrawal symptoms and who do not require immediate detoxification.

Vortioxetine [1-[2-(2,4-dimethyl-phenylsulfanyl)-phenyl]-piperazine] has the following general molecular formula:

International patent applications including WO 03/029232 and WO 2007/144005 disclose vortioxetine and pharmaceutically acceptable salts thereof. Vortioxetine was formerly referred to in the literature as LU AA 21004.

Vortioxetine is an antagonist on the 5-HT$_3$, 5-HT$_7$ and 5-HT$_{1D}$ receptors, an agonist on the 5-HT$_{1A}$ receptor and a partial agonist on the 5-HT$_{1B}$ receptor and an inhibitor of the serotonin transporter. Additionally, vortioxetine has demonstrated to enhance the levels of the neurotransmitters serotonin, noradrenalin, dopamine, acetylcholine and histamine in specific areas of the brain. All of these activities are considered to be of clinical relevance and potentially involved in the mechanism of action of the compound (*J.Med.Chem.* (2011), 54: 3206-3221; *Eur. Neuropshycopharmacol.* (2008), 18(suppl 4): S321; *Eur. Neuropshycopharmacol.* (2011), 21(suppl 4): S407-408; *Int. J. Psychiatry Clin Pract.* (2012), 5: 47).

Vortioxetine has in clinical trials shown to be a safe and efficacious treatment for depression. The results from a proof-of-concept study to evaluate the efficacy and tolerability of the compound in patients with major depressive disorder (MDD) was described by Alvares et al. A double-blind, randomized, placebo-controlled, active reference study of Lu AA 21004 in patients with major depressive disorder. *Int. J. Neuropsychopharmacol.* (2012); 15 (5): 589-600). The results from the six weeks, randomised, placebo-controlled study with approximately 100 patients in each arm show that vortioxetine separates significantly from placebo in the treatment of depressive and anxious symptoms in patients with MDD. It is also reported that no clinically relevant changes were seen in the clinical laboratory results, vital signs, weight, or ECG parameters. Results from a long-term study also show that vortioxetine is effective in preventing relapse in patients suffering from MDD (Eur. Neuropsychopharmacol. 21 (suppl 3), S396-397, 2011). A study in elderly depressed patients reported in *Int. Clin. Psychopharm.* (2012), 27: 215-227 shows that vortioxetine may be used to treat cognitive dysfunctions.

In September 2013 FDA approved vortioxetine for the treatment of major depressive disorder under the trade name Brintellix™.

Major depression, characterized by negative mood, reduced motivation, and sometimes anhedonia and decreased energy, affects nearly 5 % of people worldwide each year. Current antidepressants work well for some patients, but ~60% suffer from unresolved residual symptoms or inadequate treatment response.

In the *Diagnostic and Statistical Manual of Mental Disorders, 5th edition (DSM-V), American Psychiatric Association,* 2013; depressive disorder with melancholic features is characterized by e.g.:

A. One of the following:
 1. Loss of pleasure in all, or almost all activities;
 2. Lack of reactivity in usually pleasurable stimuli (does not feel better even when something good happens);

B. Three or more of the following:
 1. Profound despondency, despair
 2. Depression that is regularly worse in the morning
 3. Early-morning awakening
 4. Market psychomotor retardation or agitation
 5. Significant anorexia or weight loss
 6. Excessive or inappropriate guilt.

The specifier "with melancholic features" is applied if these features are present at the most severe stage of the episode. There is a near-complete absence of the capacity for pleasure, not merely a diminution. A guideline for evaluating the lack of reactivity of mood is that even highly desired events are not associated with marked brightening of mood. Either mood does not brighten at all, or it brightens only partially (e.g., up to 20%-40% of normal for only minutes at a time). The "distinct quality" of mood that is characteristic of the "with melancholic features" specifier is experienced as qualitatively different from that during a nonmelancholic depressive episode. A depressed mood that is described as merely more severe, longer lasting, or present without a reason is not considered distinct in quality. Psychomotor changes are nearly always present and are observable by others. Melancholic features exhibit only a modest tendency to repeat across episodes in the same individual. They are more frequent in inpatients, as opposed to outpatients; are less likely to occur in milder than in more severe major depressive episodes; and are more likely to occur in those with psychotic features (*Diagnostic and Statistical Manual of Mental Disorders, 5$^{th}$ edition (DSM-V), American Psychiatric Association,* 2000).

Co-morbidity of alcohol dependence and depressive disorders are common and primarily based on findings from epidemiological studies which illustrate the complexity of the comorbidity between alcohol dependence on one side and mood disorders on the other side (Grant and Hartford, *Drug and Alcohol Dependence,* (1995), Vol. 39: 197-206.; Swendsen et al., *Comprehensive Psychiatry,* (1998), Vol. 38(4): 176-184; Swendsen and Merikangas, Clin. Psychol. Rev., (2000), Vol. 20(2):173-189; Kessler et al., *Arch. Gen. Psychiatry,* (1997), Vol. 54: 313-321).

These studies have also shown that there is a high level of lifetime comorbidity between depressive disorders and alcohol dependence. Patients with depressive disorders have an increased risk of suffering from alcohol dependence compared to patients without depression. Likewise, patients with alcohol dependence have an increased risk of comorbid depressive disorders compared to patients without alcohol dependence.

A recent study estimated that 16% of depressed patients also have a diagnosable addiction disorder (Sher et al., *J. Clin. Psychiatry,* 69 (2008), pp. 907-915). Such comorbidity puts patients at greater risk. Comorbid substance use in depressed patients is associated with greater symptom severity, inadequate treatment response, poorer prognosis (including increased risk of suicide), and persistence of depressive symptoms (Thase et al., *J. Clin. Psychiatry,* 62 (Suppl. 20) (2001), pp. 32-41 and Blanco et al., *J. Clin. Psychiatry,* 73 (2012), pp. 865-873). Therefore, a tremendous need exists for pharmacotherapies effective in treating both depressive symptoms and alcohol dependence.

κ-opioid receptors and their endogenous neuropeptide ligand, dynorphin A, are densely localized in limbic and cortical areas comprising the brain reward and stress systems, and play a key role in modulating neurotransmission in these areas. In preclinical models, stress produces a prodepressive phenotype that is believed to be associated with the activation of κ-opioid receptors and subsequent downstream signaling events. Stressful effects (stress) increase the release of dynorpin, an endogenous ligand of κ-opioid receptor (Knoll and Carlezon, Brain Res. (2010), 1314: 56-73). Activation of κ-opioid receptors by dynorphin will decrease dopamine concentration in the nucleus accumbens, resulting in anhedonic symptoms of depression. A κ-opioid receptor antagonist administration will alleviate this effect.

Consistent with this hypothesis, kappa receptor agonists produce anxiogenic- and prodepressive-like effects in animals and humans (Pfeiffer A, Brantl V, Herz A, Emrich HM (1986), Science 233: 774-776 P and Todtenkopf M S, Marcus J F, Portoghese P S, and Carlezon W A Jr (2004), Psychopharmacology 172:463-470, but see also M. T. Harden, S. E. Smith, J. A. Niehoff, C. R. McCurdy, G. T. Taylor (2012), Behavioural Pharmacology, 23 (7) pp. 710-

715, whereas kappa receptor antagonists reliably exhibit antidepressant-like effects in animal models predictive of efficacy in the domains of mood and affect (Mague S D, Pliakas A M, Todtenkopf M S, Tomasiewicz H C, Zhang Y, Stevens W C Jr, Jones R M, Portog-hese P S, and Carlezon W A Jr (2003), J Pharmacol Exp Ther 305:323-330; B. B. Land, M. R. Bruchas, S. Schattauer, W. J. Giardino, M. Aita, D. Messinger (2009), PNAS 106 (45) pp. 19168-19173 and Carr G V, Bangasser D A, Bethea T, Young M, Valentino R J, Lucki I (2010), Neuropsycho-pharmacology 35:752-763).

While some opioid antagonists are efficacious in animal models of alcoholism, they do not produce reliable antidepressant- or anxiolytic-like effects in animals or humans, likely due to functional opposition between mu and kappa receptors. Similarly, antidepressants are weakly and inconsistently effective at reducing alcohol consumption in depressed patients with comorbid addictive disorders. Because kappa antagonists demonstrate efficacy in animal models predictive of efficacy in mood and addictive disorders, they have the potential to treat depressed patients with comorbid alcohol dependence.

There is a need for new treatments for use in patients with depressive disorder with melancholic features. Furthermore, there is a need for new treatments for use in patients with alcohol dependence who have depressive disorder with melancholic features. In particular, there is a need for new treatments which could give rise to advantages such as e.g. improved efficacy and/or a different side effect profile compared to existing treatments.

SUMMARY OF THE INVENTION

The present invention relates to an opioid antagonist with κ-opioid receptor activity for treatment of depressive disorder with melancholic features.

The invention further relates to an opioid antagonist with κ-opioid receptor activity for use in treatment of depressive disorder with melancholic features, wherein said use comprises the following steps:
a) identifying a patient with depressive disorder with melancholic features, and
b) administering a therapeutically effective amount of said opioid antagonist with κ-opioid receptor activity and optionally a therapeutically effective amount of vortioxetine to the patient identified in step a).

The invention further relates to an opioid antagonist with κ-opioid receptor activity and vortioxetine for treatment of depressive disorder with melancholic features.

The invention further relates to a pharmaceutical composition comprising an opioid antagonist with κ-opioid receptor activity and vortioxetine together with a pharmaceutically acceptable excipient.

BRIEF DESCRIPTION OF DRAWINGS

X-axis: weeks of treatment; Y-axis: sucrose intake (g). Values are means +/−SEM.

FIG. 1.

Effects of chronic treatment with vehicle and imipramine (10 mg/kg, IP, once daily).
○=control/vehicle; ◇=control/imipramine; ●=stressed/vehicle; ◆=stressed/imipramine.
*–$p<0.05$, –$<0.01$, *–$p<0.001$; relative to vehicle- or drug-treated control groups.
–$p<0.05$, ##–$p<0.01$, ###–$p<0.001$; relative to drug-treated stressed animals at Week 0.

FIG. 2.

Effects of chronic treatment with vehicle, vortioxetine (10 mg/kg, IP, once daily), nalmefene (1 mg/kg, IP, once daily) and joint administration of both drugs.
○=control/vehicle; △=control/vortioxetine; ◇=control/nalmefene;
▽=control/vortioxetine+nalmefene; ●=stressed/vehicle;
▲=stressed/vortioxetine;
◆=stressed/nalmefene; ▼=stressed/vortioxetine+nalmefene.
–$p<0.01$, *–$p<0.001$; relative to vehicle- or drug-treated control groups.
–$p<0.05$, ##–$p<0.01$, ###–$p<0.001$; relative to drug-treated stressed animals at Week 0.

Definitions

Throughout the specification "opioid receptor antagonists with κ-opioid receptor activity", "opioid antagonists with κ-opioid receptor activity", "opioid receptor antagonists with κ-activity" and "opioid antagonists with κ-activity" are used interchangeably. All are intended to include opioid antagonists with κ-activity selected from, but not limited to: nalmefene, naltrexone, naloxone, nor-BNI (nor-binaltorphimine), buprenorphine, naltriben, nalorphine, levallorphan, LY 2456302 ((S)-3-fluoro4-(4-((2-(3,5-dimethylphenyl)pyrrolidin-1-yl)methyl)phenoxy)benzamide), dynorphin, JDTic ((3R)-7-Hydroxy-N-{(1S)-1-{[(3R,4R)-4-(3-hydroxyphenyl)-3,4-dimethyl-1-piperidinyl]methyl}-2-methylpropyl}-1,2,3,4-tetrahydro-3-isoquinoline-carboxamide), and other opioid antagonists with κ-activity. In one embodiment, opioid antagonists with κ-activity of the present invention are selected from nalmefene, naltrexone, naloxone, nor-BNI (nor-binaltorphimine), buprenorphine, nalorphine and levallorphan. Particular mention is made of nalmefene.

Throughout the specification, the term "nalmefene" is intended to include any form of the compound, such as the free base and pharmaceutically acceptable salts. The free base and pharmaceutically acceptable salts include anhydrous forms and solvated forms such as hydrates. The anhydrous forms include amorphous and crystalline forms, and the solvates include crystalline forms. In a particular embodiment, nalmefene is in the form of a hydrochloride salt. In a more particular embodiment, nalmefene is in the form of the hydrochloride dihydrate. Throughout the description, when a dose is specified for nalmefene, said dose is calculated as the free base, i.e. when the nalmefene dose is 18 mg this corresponds to 18 mg of nalmefene free base.

Throughout the specification, the term "vortioxetine" is intended to include any form of the compound, such as the free base and pharmaceutically acceptable salts. Particular mention is made of the HBr salt and the (DL)-lactate salt. Throughout the description, when a dose is specified for vortioxetine, said dose is calculated as the free base, i.e. when the vortioxetine dose is 10 mg this corresponds to 10 mg of vortioxetine free base.

In the present context, pharmaceutical carriers and pharmaceutical excipients include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier may include any sustained release material known in the art, such as glyceryl monostearate or glyceryl distearate, alone or mixed with a wax.

In the present context, "Pharmaceutical composition" refers to a dose form for example an oral dose form, such as a solid oral dose form, typically tablets or capsules. "Pharmaceutical compositions of the present invention" refers to all pharmaceutical compositions covered by the claims and description.

In the present context, a "unit dosage form" refers to a formulation unit of a pharmaceutical composition e.g. one tablet or one capsule.

In the present context, when one compound (e.g. an opioid antagonist with κ-activity, such as nalmefene) is used in combination with another compound (e.g. vortioxetine), this indicates in one embodiment that said two compounds can be administrated simultaneously for example in a pharmaceutical composition comprising both compounds. In another embodiment, when one compound (e.g. an opioid antagonist with κ-activity, such as nalmefene) is used in combination with another compound (e.g. vortioxetine), this indicates that said two compounds are administered separately in suitable individual pharmaceutical compositions. These individual compositions may be administered simultaneously e.g. with regular intervals once daily either morning or evening, or they may be administered independently e.g. one compound with regular intervals once daily in the morning and the other compound with regular intervals once daily in the evening.

In the present context, when an opioid antagonist with κ-activity (e.g. nalmefene) is used as "stand-alone treatment", this indicates that said opioid antagonist with κ-activity is not used in combination with vortioxetine in the treatment of depressive disorder with melancholic features i.e. said opioid antagonist with κ-activity is used in a patient who is not in treatment with vortioxetine.

A "therapeutically effective amount" of compounds as used herein means an amount sufficient to cure, alleviate or partially arrest the clinical manifestations of a given disease and its complications in a therapeutic intervention comprising the administration of said compounds. An amount adequate to accomplish this is defined as "a therapeutically effective amount". The "therapeutically effective amount" will vary depending on, inter alia, the disease and its severity, and on the age, weight, physical condition and responsiveness of the patient to be treated. The "therapeutically effective amount" will also vary depending on the choice of opioid antagonist with κ-activity, both when the opioid antagonist with κ-activity is used as stand-alone treatment and when the opioid antagonist with κ-activity is used in combination with vortioxetine. The "therapeutically effective amount" of an opioid antagonist with κ-activity may further vary depending on whether the opioid antagonist with κ-activity is used in combination with vortioxetine or as stand-alone treatment. Furthermore, the "therapeutically effective amount" may vary if the opioid antagonist with κ-activity, or the opioid antagonist with κ-activity and vortioxetine, are combined with one or more other compounds.

In the present context, "treatment" and "treating" refers to the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relieve the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. In one aspect of the present invention, "treatment" and "treating" refers to prophylactic (preventive) treatment. In another aspect, "treatment" and "treating" refers to (curative) treatment. The patient to be treated is preferably a mammal, in particular a human being.

The term "depressive disorder with melancholic features" is described e.g. in the $5^{th}$ edition of the Diagnostic and Statistical Manual of Mental Disorders (*Diagnostic and Statistical Manual of Mental Disorders, 5th edition (DSM-V), American Psychiatric Association*, 2013). The term "depressive disorder with melancholic features" is characterized herein by e.g.:

A. One of the following:
  1. Loss of pleasure in all, or almost all activities;
  2. Lack of reactivity in usually pleasurable stimuli (does not feel better even when something good happens);

B. Three or more of the following:
  1. Profound despondency, despair
  2. Depression that is regularly worse in the morning
  3. Early-morning awakening
  4. Market psychomotor retardation or agitation
  5. Significant anorexia or weight loss
  6. Excessive or inappropriate guilt The specifier "with melancholic features" is applied if these features are present at the most severe stage of the episode.

The terms "anhedonia" and "anhedonic symptom" are used interchangeably and is defined as the inability to experience pleasure from activities usually found enjoyable, e.g. exercise, hobbies, music, sexual activities or social interactions. The terms "anhedonia" and "anhedonic symptom" are closely related to criterion A.1. in the above definition of "depressive disorder with melancholic features" and is throughout the description used in relation to description of pre-clinical experiments.

The term "treatment of depressive disorder with melancholic features" comprises treatment of both the depressive disorder and melancholic features associated herewith.

The term "alcohol dependence" is a commonly known term for a skilled person described e.g. in the revised $4^{th}$ edition of the Diagnostic and Statistical Manual of Mental Disorders (DSM-IV-TR) (*Diagnostic and Statistical Manual of Mental Disorders, $4^{th}$ edition text revision*, American Psychiatric Publishing, 2000). As used herein, the term "alcohol dependence" is defined as the presence of three or more of the seven areas of life impairment related to alcohol in the same 12-month period. These impairments include 1) tolerance, 2) withdrawal, 3) the alcohol is often taken in larger amounts or over a longer period than was intended, 4) persistent desire or unsuccessful efforts to cut down or control alcohol intake, 5) a great deal of time is spent in activities necessary to obtain alcohol, intake alcohol, or recover from its effects, 6) important social, occupational, or recreational activities are given up or reduced because of alcohol consumption, 7) alcohol use is continued despite knowledge of having a persistent or recurrent physical or psychological problem that is likely to have been caused or exacerbated by alcohol consumption.

DETAILED DESCRIPTION OF THE INVENTION

The inventors of the present invention, have identified that an opioid antagonist with κ-activity (nalmefene) is effective in a model for chronic mild stress (CMS) indicating that an opioid antagonist with κ-activity can be used for treatment of depressive disorder with melancholic features. The inventors furthermore identified that when combining said opioid antagonist with κ-activity (nalmefene) with vortioxetine in said CMS model, a faster onset of action was achieved (Example 1).

Thus, the present invention relates to an opioid receptor antagonist with κ-opioid receptor activity for use in treatment of depressive disorder with melancholic features.

The invention further relates to an opioid antagonist with κ-opioid receptor activity for use in combination with vortioxetine for treatment of depressive disorder with melancholic features.

The invention further relates to an opioid antagonist with κ-opioid receptor activity for use in treatment of depressive disorder with melancholic features, wherein said use comprises the following steps:
a) identifying a patient with depressive disorder with melancholic features, and
b) administering a therapeutically effective amount of said opioid antagonist with κ-opioid receptor activity and optionally a therapeutically effective amount of vortioxetine to the patient identified in step a).

The invention further relates to a pharmaceutical composition comprising an opioid antagonist with κ-opioid receptor activity and vortioxetine together with a pharmaceutically acceptable excipient.

In one embodiment, said opioid antagonist with κ-activity is selected from nalmefene, naloxone, naltrexone, nor-BNI, buprenorphine, nalorphine and levallorphan which are all known compounds to the person skilled in the art and available by direct purchase and/or from methods for preparation known in the art.

In a preferred embodiment, said opioid antagonist with κ-activity is nalmefene.

Assessment of the effect of an opioid antagonist with κ-activity as stand-alone treatment and in combination with vortioxetine on the treatment of depressive disorder with melancholic features, particularly the effect on anhedonia, has been performed by testing nalmefene and a combination of nalmefene and vortioxetine in the sucrose preference test (chronic mild stress) as outlined in Example 1. Nalmefene was effective in the CMS model, while Vortioxetine was not effective in the CMS model when administered alone. Injection of both vortioxetine and nalmefene gave a faster onset in the model than nalmefene administered alone.

Further non-clinical models for assessment of the effect in treatment of depressive disorder with melancholic features are the Progressive Ratio responding for a natural reinforcer, and/or the Intracranial self-stimulation (ICSS) test in rodents as outlined in Examples 2-3.

According to the present invention, the opioid antagonist with κ-activity and optionally vortioxetine or a pharmaceutically acceptable salt of any of these two compounds may be administered in any suitable way, e.g. orally, transmucosally or parenterally, and the opioid antagonist with κ-activity and/or vortioxetine may be presented in any suitable form for such administration. In one embodiment, and in accordance with the purpose of the present invention, the opioid antagonist with κ-activity and optionally vortioxetine are both administered in the form of solid pharmaceutical entities, suitably as tablets or capsules or in the form of suspensions, solutions or dispersions for injection.

The pharmaceutical compositions according to the invention may be formulated with pharmaceutically acceptable carriers or diluents as well as any other known adjuvants and excipients in accordance with conventional techniques such as those disclosed in Remington: *The Science and Practice of Pharmacy*, 21 Edition, Hauber, Ed., Lippincott Williams & Wilkins, 2006. Tablets may thus be prepared by mixing the active ingredients with an ordinary carrier, such as an adjuvant and/or diluent, and subsequently compressing the mixture in a tableting machine.

Suitable pharmaceutical carriers and excipients include inert solid diluents or fillers, sterile aqueous solution and various organic solvents. Non-limiting examples of solid carriers are corn starch, lactose, terra alba, sucrose, cyclodextrin, talcum, gelatine, agar, pectin, acacia, magnesium stearate, stearic acid and lower alkyl ethers of cellulose. Non-limiting examples of liquid carriers are syrup, peanut oil, olive oil, phospholipids, fatty acids, fatty acid amines, polyoxyethylene and water.

Any other adjuvant or additive such as colorings, aroma, and preservatives may also be used provided that they are compatible with the active ingredients. The pharmaceutical compositions of the invention thus typically comprise an effective amount of an opioid antagonist with κ-activity and/or vortioxetine and one or more pharmaceutically acceptable carrier.

The pharmaceutical compositions formed by combining a compound used in the invention and the pharmaceutical acceptable carriers are then readily administered in a variety of dosage forms suitable for the disclosed routes of administration.

The active pharmaceutical ingredients used the present invention, i.e. an opioid antagonist with κ-activity and optionally vortioxetine, may be administered alone as pure compounds or in combination with pharmaceutically acceptable carriers or excipients, in either single or multiple doses.

The pharmaceutical compositions may be specifically formulated for administration by any suitable route such as the oral, rectal, nasal, pulmonary, topical (including buccal and sublingual), transdermal and parenteral (including subcutaneous, intramuscular, intravenous, intraperitoneal and intradermal) route, the oral route being preferred. It will be appreciated that the preferred route may depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups, drops and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, creams, gels, inhalants, dermal patches, implants, etc.

For parenteral administration, solutions of the compounds in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be in form of a tablet or placed in a hard gelatine capsule, in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing an active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

A suitable oral formulation of nalmefene is described in WO 2012/059103. A suitable oral formulation of vortioxetine is described in WO 2011/136376.

When simultaneous administration of an opioid antagonist with κ-activity and vortioxetine is envisaged, a composition containing both the opioid antagonist with κ-activity and vortioxetine may be particularly convenient. Alternatively, the opioid antagonist with κ-activity and vortioxetine may be administered separately in the form of suitable compositions. The compositions may be prepared as described hereinabove. In one embodiment of the invention, separate unit forms of the opioid antagonist with κ-activity and vortioxetine are administered simultaneously e.g. both compounds are administered with regular intervals once daily either morning or evening. In another embodiment, separate unit forms of the opioid antagonist with κ-activity and vortioxetine are administered independently e.g. vortioxetine are administered with regular intervals once daily in the morning and the opioid antagonist with κ-activity with regular intervals once daily in the evening or vice versa.

The present invention also comprises a kit comprising discrete unit dosage forms containing an opioid antagonist with κ-activity and discrete unit dosage forms containing vortioxetine, all contained in the same container or pack, e.g. a blister pack.

Pharmaceutical compositions and kits according to the invention preferably comprises an opioid antagonist with κ-activity and/or vortioxetine in therapeutically effective amounts. A daily dose of nalmefene is preferably between 1 and 30 mg, more preferably between 5 and 20 mg such as 18 mg. A daily dose of vortioxetine is preferably between 1 and 30 mg, more preferably between 5 and 20 mg such as 5, 10, 15 or 20 mg.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the various aspects, embodiments, implementations and features of the invention mentioned herein may be claimed separately, or in any combination.

Embodiments According to the Invention

In the following, embodiments of the invention are disclosed. The first embodiment is denoted E1, the second embodiment is denoted E2 and so forth.

E1. An opioid antagonist with κ-activity and vortioxetine for use in treatment of depressive disorder with melancholic features.

E2. An opioid antagonist with κ-activity and vortioxetine for use in treatment of depressive disorder with melancholic features, wherein said use comprises the following steps;
  a) identifying a patient with depressive disorder with melancholic features, and
  b) administering therapeutically effective amounts of said opioid antagonist with κ-activity and vortioxetine to the patient identified in step a).

E3. The opioid antagonist with κ-activity and vortioxetine according to any of embodiments 1-2, wherein said opioid antagonist with κ-activity is selected from nalmefene, naloxone, naltrexone, nor-BNI, buprenorphine, nalorphine and levallorphan.

E4. The opioid antagonist with κ-activity and vortioxetine according to embodiment 3, wherein said opioid antagonist with κ-activity is nalmefene.

E5. Nalmefene and vortioxetine according to embodiment 4, wherein the dose of nalmefene is between 1 and 30 mg.

E6. Nalmefene and vortioxetine according to embodiment 5, wherein the dose of nalmefene is between 5 and 20 mg.

E7. Nalmefene and vortioxetine according to embodiment 6, wherein the dose of nalmefene is 18 mg.

E8. The opioid antagonist with κ-activity and vortioxetine according to any of embodiments 1-7, wherein the dose of vortioxetine is between 1 and 30 mg.

E9. The opioid antagonist with κ-activity and vortioxetine according to embodiment 8, wherein the dose of vortioxetine is between 5 and 20 mg.

E10. The opioid antagonist with κ-activity and vortioxetine according to embodiment 9, wherein the dose of vortioxetine is 5, 10, 15 or 20 mg.

E11. The opioid antagonist with κ-activity and vortioxetine according to any of embodiments 1-10, wherein said opioid antagonist with κ-activity and vortioxetine are administered simultaneously.

E12. The opioid antagonist with κ-activity and vortioxetine according to any of embodiments 1-10, wherein said opioid antagonist with κ-activity and vortioxetine are administered independently.

E13. The opioid antagonist with κ-activity and vortioxetine according to any of embodiments 1-12, wherein said opioid antagonist with κ-activity and vortioxetine are contained in separate unit dosage forms.

E14. The opioid antagonist with κ-activity and vortioxetine according to any of embodiments 1-11, wherein said opioid antagonist with κ-activity and vortioxetine are contained in the same unit dosage form.

E15. The opioid antagonist with κ-activity and vortioxetine according to any of embodiments 1-14 wherein said treatment comprises treatment of both depressive disorder with melancholic features and treatment of alcohol dependence.

E16. An opioid antagonist with κ-activity for use in treatment of depressive disorder with melancholic features.

E17. An opioid antagonist with κ-activity for use in treatment of depressive disorder with melancholic features, wherein said use comprises the following steps;
  a) identifying a patient with depressive disorder with melancholic features, and
  b) administering a therapeutically effective amount of said opioid antagonist with κ-activity to the patient identified in step a).

E18. The opioid antagonist with κ-activity according to any of embodiments 16-17, wherein said opioid antagonist with κ-activity is used as stand-alone treatment in the treatment of depressive disorder with melancholic features.

E19. The opioid antagonist with κ-activity according to embodiment 16, wherein said opioid antagonist with κ-activity is used in combination with vortioxetine in the treatment of depressive disorder with melancholic features.

E20. The opioid antagonist with κ-activity according to embodiment 17, wherein said opioid antagonist with κ-activity according is used in combination with vortioxetine in the treatment of depressive disorder with melancholic features; wherein step b) further comprises administering a therapeutically effective amount of vortioxetine to the patient identified in step a).

E21. The opioid antagonist with κ-activity according to any of embodiments 16-20, wherein said opioid antagonist with κ-activity is selected from nalmefene, naloxone, naltrexone, nor-BNI, buprenorphine, nalorphine and levallorphan.

E22. The opioid antagonist with κ-activity according to embodiment 21, wherein said opioid antagonist with κ-activity is nalmefene.

E23. Nalmefene according to embodiment 22, wherein the dose of nalmefene is between 1 and 30 mg.

E24. Nalmefene according to embodiment 23, wherein the dose of nalmefene is between 5 and 20 mg.

E25. Nalmefene according to embodiment 24, wherein the dose of nalmefene is 18 mg.

E26. The opioid antagonist with κ-activity used in combination with vortioxetine according to any of embodiments 19-25, wherein the dose of vortioxetine is between 1 and 30 mg.

E27. The opioid antagonist with κ-activity used in combination with vortioxetine according to embodiment 26, wherein the dose of vortioxetine is between 5 and 20 mg.

E28. The opioid antagonist with κ-activity used in combination with vortioxetine according to embodiment 27, wherein the dose of vortioxetine is 5, 10, 15 or 20 mg.

E29. The opioid antagonist with κ-activity used in combination with vortioxetine according to any of embodiments 19-28, wherein said opioid antagonist with κ-activity and vortioxetine are administered simultaneously.

E30. The opioid antagonist with κ-activity used in combination with vortioxetine according to any of embodiments 19-28, wherein said opioid antagonist with κ-activity and vortioxetine are administered independently.

E31. The opioid antagonist with κ-activity used in combination with vortioxetine according to any of embodiments 19-30, wherein said opioid antagonist with κ-activity and vortioxetine are contained in separate unit dosage forms.

E32. The opioid antagonist with κ-activity used in combination with vortioxetine according to any of embodiments 19-29, wherein said opioid antagonist with κ-activity and vortioxetine are contained in the same unit dosage form.

E33. The opioid antagonist with κ-activity according to any of embodiments 16-32, wherein said treatment comprises treatment of both depressive disorder with melancholic features and treatment of alcohol dependence.

E34. A method for the treatment of depressive disorder with melancholic features, the method comprising administration of a therapeutically effective amount of an opioid antagonist with κ-activity to a patient in need thereof.

E35. A method for the treatment of depressive disorder with melancholic features comprising the following steps;
  a) identifying a patient with depressive disorder with melancholic features, and
  b) administering a therapeutically effective amount of an opioid antagonist with κ-activity to the patient identified in step a).

E36. The method according to any of embodiments 34-35, wherein said opioid antagonist with κ-activity is used as stand-alone treatment in the treatment of depressive disorder with melancholic features.

E37. The method according to embodiment 34, wherein said method further comprises administration of a therapeutically effective amount of vortioxetine.

E38. The method according to embodiment 35, wherein step b) further comprises administering a therapeutically effective amount of vortioxetine to the patient identified in step a).

E39. The method according to any of embodiments 34-38, wherein said opioid antagonist with κ-activity is selected from nalmefene, naloxone, naltrexone, nor-BNI, buprenorphine, nalorphine and levallorphan.

E40. The method according to embodiment 39, wherein said opioid antagonist with κ-activity is nalmefene.

E41. The method according to embodiment 40, wherein said therapeutically effective amount nalmefene is between 1 and 30 mg.

E42. The method according to embodiment 41, wherein said therapeutically effective amount of nalmefene is between 5 and 20 mg.

E43. The method according to embodiment 42, wherein said therapeutically effective amount of nalmefene is 18 mg.

E44. The method according to any of embodiments 37-43, wherein said therapeutically effective amount of vortioxetine is between 1 and 30 mg.

E45. The method according to embodiment 44, wherein said therapeutically effective amount of vortioxetine is between 5 and 20 mg.

E46. The method according to embodiment 45, wherein said therapeutically effective amount of vortioxetine is 5, 10, 15 or 20 mg.

E47. The method according to any embodiments 37-46, wherein said opioid antagonist with κ-activity and vortioxetine are administered simultaneously.

E48. The method according to any embodiments 37-46, wherein said opioid antagonist with κ-activity and vortioxetine are administered independently.

E49. The method according to any of embodiments 37-48, wherein said said opioid antagonist with κ-activity and vortioxetine are contained in separate unit dosage forms.

E50. The method according to any of embodiments 37-47, wherein said opioid antagonist with κ-activity and vortioxetine are contained in the same unit dosage form.

E51. The method according to any of embodiments 34-50, wherein said treatment comprises treatment of both depressive disorder with melancholic features and treatment of alcohol dependence.

E52. Use of an opioid antagonist with κ-activity for the manufacture of a medicament for treatment of depressive disorder with melancholic features.

E53. Use of an opioid antagonist with κ-activity for the manufacture of a medicament for treatment of depressive disorder with melancholic features in a patient, wherein said patient has been diagnosed with a depressive disorder with melancholic features.

E54. The use according to any of embodiments 52-53, wherein said medicament further comprises vortioxetine.

E55. The use according to any of embodiments 52-54, wherein said opioid antagonist with κ-activity is selected from nalmefene, naloxone, naltrexone, nor-BNI, buprenorphine, nalorphine and levallorphan.

E56. The use according to embodiment 55, wherein said opioid antagonist with κ-activity is nalmefene.

E57. The use according to embodiment 56, wherein said medicament comprises 1-30 mg of nalmefene.

E58. The use according to embodiment 57, wherein said medicament comprises 5-20 mg of nalmefene.

E59. The use according to embodiment 58, wherein said medicament comprises 18 mg of nalmefene.

E60. The use according to any of embodiments 54-59, wherein said medicament comprises 1-30 mg of vortioxetine.

E61. The use according to embodiment 60, wherein said medicament comprises 5-20 mg of vortioxetine.

E62. The use according to embodiment 61, wherein said medicament comprises 5, 10, 15 or 20 mg of vortioxetine.

E63. The use according to any of embodiments 52-62, wherein said treatment comprises treatment of both depressive disorder with melancholic features and treatment of alcohol dependence.

E64. A pharmaceutical composition comprising an opioid antagonist with κ-activity and vortioxetine, together with a pharmaceutically acceptable excipient.

E65. The pharmaceutical composition according to embodiment 64, wherein said opioid antagonist with κ-activity is selected from nalmefene, naloxone, naltrexone, nor-BNI, buprenorphine nalorphine and levallorphan.

E66. The pharmaceutical composition according to embodiment 65, wherein said opioid antagonist with κ-activity is nalmefene.

E67. The pharmaceutical composition according to embodiment 66, comprising 1-30 mg of nalmefene.

E68. The pharmaceutical composition according to embodiment 67, comprising 5-20 mg of nalmefene.

E69. The pharmaceutical composition according to embodiment 68, comprising 18 mg of nalmefene.

E70. The pharmaceutical composition according to any of embodiments 64-69, comprising 1-30 mg vortioxetine.

E71. The pharmaceutical composition according to embodiment 70, comprising 5-20 mg vortioxetine.

E72. The pharmaceutical composition according to embodiment 71, omprising 5, 10, 15 or 20 mg vortioxetine.

E73. The pharmaceutical composition according to any of embodiments 64-72, comprising 5-20 mg of nalmefene and 5-20 mg of vortioxetine.

E74. A kit comprising an opioid antagonist with κ-activity together with vortioxetine.

E75. The kit according to embodiment 74, wherein said opioid antagonist with κ-activity is selected from nalmefene, naloxone, naltrexone, nor-BNI, buprenorphine, nalorphine and levallorphan.

E76. The kit according to embodiment 75, wherein said opioid antagonist with κ-activity is nalmefene.

E77. The kit according to any of embodiments 74-76, which is adapted for simultaneous administration of said opioid antagonist with κ-activity and vortioxetine.

E78. The kit according to any of embodiments 74-76, which is adapted for independent administration of said opioid antagonist with κ-activity and said vortioxetine.

EXAMPLES

Assessment of an opioid antagonist with κ-activity (nalmefene) and vortioxetine for the treatment effect on anhedonia was performed in the Chronic mild stress model (CMS) as outlined in Example 1.

Example 1

Sucrose Preference Test (Chronic Mild Stress Model (CMS))

Rodents inherently have an interest in sweet foods or liquids. Exposure to stressfull conditions reduces the interest for sweet foods or solutions, indicating a reduced sensitivity to rewards. This can be assessed for example in a sucrose preference test, where the stress-induced reduction of intake of a sucrose solution is used as a measure of anhedonia (reduces sensitivity to rewards). This stress-induced reduction of sucrose intake in the rat is a well-established animal model of anhedonia (Nielsen, Arnt and Sánchez. Intracranial self-stimulation and sucrose intake differ as hedonic measures following chronic mild stress: interstrain and interindividual differences. *Behav. Brain. Res.* (2000), 107 (1-2): 21-33).

Materials and Methods

Animals.

Male Wistar rats (Charles River, Germany) were brought into the laboratory one month before the start of the experiment. Except as described below, the animals were singly housed with food and water freely available, and were maintained on a 12-h light/dark cycle (lights on at 08.00) and in a constant temperature (22±2° C.) and humidity (50±5%) conditions. All procedures used in this study are conformed to the rules and principles of the 86/609/EEC Directive, and were approved by the Local Bioethical Committee at the Institute of Pharmacology, Polish Academy of Sciences, Krakow, Poland.

Stress Procedure.

After a period of 3 weeks of adaptation to laboratory and housing conditions, the animals were trained to consume a 1% sucrose solution; training consisted of nine 1 h baseline tests in which sucrose was presented, in the home cage, following 14 h food and water deprivation. The sucrose intake was measured by weighing pre-weighed bottles containing the sucrose solution, at the end of the test. Subsequently, sucrose consumption was monitored, under similar conditions, at weekly intervals throughout the whole experiment.

On the basis of their sucrose intakes in the final baseline test, the animals were divided into two matched groups. One group of animals was subjected to the chronic mild stress procedure for a period of 8 consecutive weeks. Each week of stress regime consisted of: two periods of food or water deprivation, two periods of 45 degree cage tilt, two periods of intermittent illumination (lights on and off every 2 h), two periods of soiled cage (250 ml water in sawdust bedding), one period of paired housing, two periods of low intensity stroboscopic illumination (150 flashes/min), and three periods of no stress. All stressors were 10-14 h of duration and were applied individually and continuously, day and night. Control animals were housed in separate rooms and had no contact with the stressed animals. They were deprived of food and water for 14 h preceding each sucrose test, but otherwise food and water were freely available in the home cage.

Drug Administration.

On the basis of their sucrose intakes following 2 weeks of initial stress, both stressed and control groups were each divided further into matched subgroups (n=8), and for subsequent five weeks they received daily IP administration of vehicle (0.9% saline, 1 ml/kg), Vortioxetine (10 mg/kg), Nalmefene (1 mg/kg), joint injections of Vortioxetine (10 mg/kg) and Nalmefene (1 mg/kg) or imipramine HCl (10 mg/kg) as the reference treatment. The volume of all injections was 1 ml/kg. The drugs were administered at approx. 10.00 and the weekly sucrose tests were carried out 24 h following the last drug injections. After five weeks all treatments were terminated and one additional sucrose test was carried out following one week of withdrawal. Stress was continued throughout the entire period of treatment and withdrawal.

Statistics.

All results obtained in this study were analysed (Statistica for Windows v. 6.0) by multiple analyses of variance with three between-subjects factors (stress/control, drug treatments and successive sucrose tests). The Fisher's LSD test was used for post-hoc comparisons of means.

Results

Chronic mild stress caused a gradual decrease in the consumption of 1% sucrose solution. In the final baseline test, all animals drank approximately 13 g of sucrose solution. Following initial two weeks of stress, intakes remained at similar level in controls but fell to approximately 7 g in stressed animals, resulting in a significant Group effect [$F(1,76)=113.835$; $p<0.001$]. Such a difference between control and stressed vehicle-treated animals persisted at similar level for the remainder of the experiment (see FIGS. 1 and 2).

Figure 1:
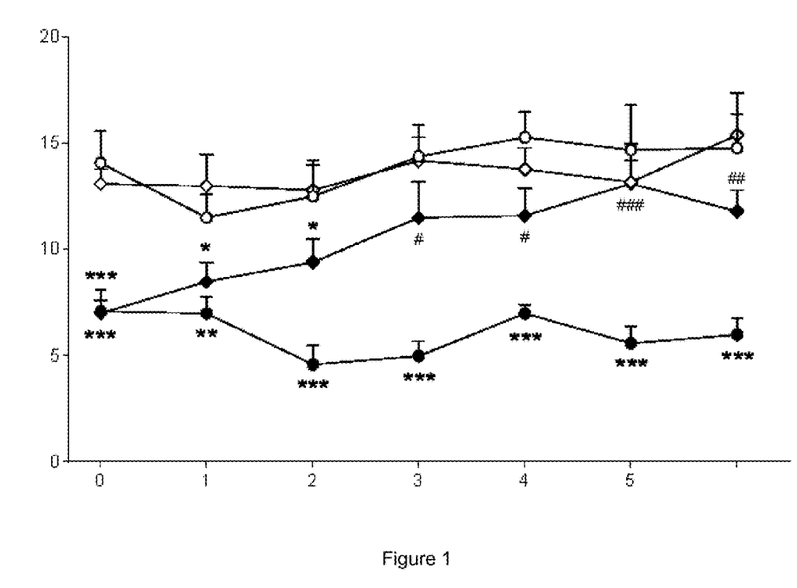
FIGS. 1 and 2 illustrate the effect of vehicle and test compounds on chronic mild stress in male Wistar rats (control rats and rats exposed to chronic mild stress).

Imipramine in CMS (FIG. 1)

Imipramine was used as a positive control. Effects of chronic treatment with vehicle and imipramine (10 mg/kg, IP, once daily) on the consumption of 1% sucrose solution in controls (open symbols) and in animals exposed to chronic mild stress (closed symbols). Treatment commenced following 2 weeks of initial stress. Values are means +/−SEM.

As compared to vehicle administration, imipramine had no significant effect on sucrose intakes in control animals [$F(1,84)=0.219$; NS] and gradually increased the sucrose consumption in stressed animals, resulting in a significant Treatment effect [$F(1,84)=51.676$; $p<0.001$] and Treatment× Weeks interaction [$F(5,84)=4.286$; $p<0.01$].

As compared to Week 0 scores, the increase in sucrose intakes in stressed animals administered imipramine reached statistical significance after three weeks of treatment ($p=0.013$) and this effect was enhanced on the following weeks and after one week of withdrawal from imipramine treatment.

*−$p<0.05$, −$p<0.01$, *−$p<0.001$; relative to vehicle- or drug-treated control groups.

−$p<0.05$, ##−$p<0.01$, ###−$p<0.001$; relative to drug-treated stressed animals at Week 0.

Figure 2:
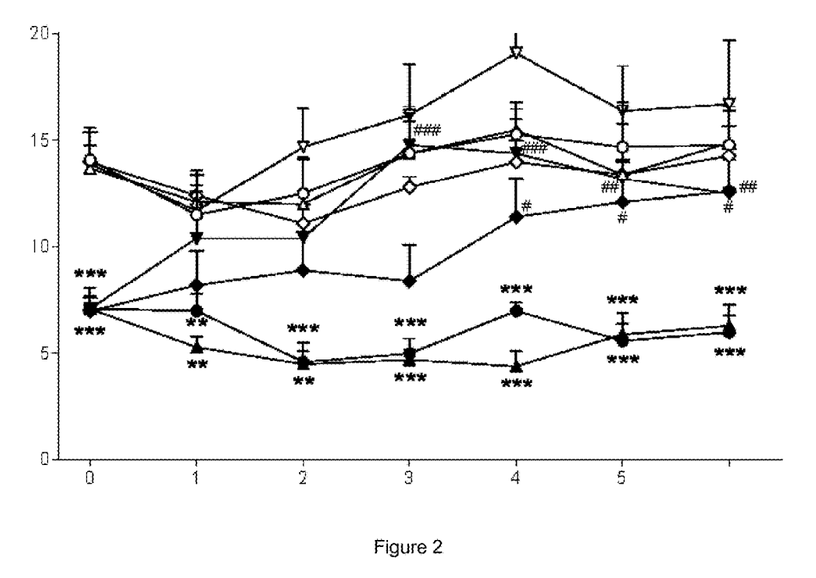

Vortioxetine and Nalmefene in CMS (FIG. 2)

Effects of chronic treatment with vehicle, Vortioxetine (10 mg/kg, IP), Nalmefene (1 mg/kg, IP) and joint injections of both drugs on the consumption of 1% sucrose solution in controls (open symbols) and in animals exposed to chronic mild stress (closed symbols). Treatment commenced following 2 weeks of initial stress. Values are means +/−SEM. As compared to vehicle administration, Vortioxetine had no significant effect on sucrose intakes in either the control [$F(1,84)=0.069$; NS] or the stressed [$F(1,84)=2.979$; NS] animals. Nalmefene had no effect on sucrose intakes in control animals [Treatment effect: $F(1,84)=1.169$; NS] and gradually increased the sucrose consumption in stressed animals, resulting in a significant Treatment effect [$F(1,84)=19.986$; $p<0.001$] but not Treatment×Weeks interaction [$F(5,84)=1.760$; NS]. This was probably caused by the fact that two stressed animals receiving Nalmefene did not respond to the drug, increasing the SEMs.

The joint administration of Vortioxetine and Nalmefene did not significantly increase the intakes in control animals [Treatment effect: $F(1,84)=2.453$; NS] and caused a highly significant Treatment effect [$F(1,84)=78.050$; $p<0.001$] and Treatment×Weeks interaction [$F(5,84)=4.886$; $p<0.001$] in stressed animals.

As compared to Week 0 scores, the increase in sucrose intakes in stressed animals administered Nalmefene reached statistical significance after four weeks of treatment ($p=0.043$) and this effect was maintained on the following week. The increase of intakes caused by Nalmefene administered together with Vortioxetine was apparent after already first week of treatment, reached significance after three weeks ($p<0.001$) and was maintained thereafter. In all groups the intakes were maintained at similar level one week after cessation of treatment.

−$p<0.01$, *−$p<0.001$; relative to vehicle- or drug-treated control groups.

−$p<0.05$, ##−$p<0.01$, ###−$p<0.001$; relative to drug-treated stressed animals at Week 0.

Before the stress procedure was initiated (Baseline) the control and to-be-stressed animals had similar body weights (326 and 321 g, respectively) and after initial two weeks of stress (Week 0) this pattern did not change (347 vs 341 g, respectively). As compared to vehicle-treated group, imipramine and vortioxetine decreased the body weight of control [IMI: $F(1,14)=9.040$; $p<0.05$, Vortioxetine: $F(1,14)=7.473$; $p<0.05$] and stressed [IMI: $F(1,14)=4.049$; NS, Vortioxetine: $F(1,14)=3.310$; NS] animals. Nalmefene alone did not affect the body weights [Ctr: $F(1,14)=0.226$; NS, Str:

F(1,14)=0.001; NS]. Vortioxetine administered together with Nalmefene decreased body weights of control [F(1,14)=7.862; p<0.05] and stressed [F(1,14)=1.107; NS] animals.

TABLE 1

Body weights (g) after five weeks of treatment (means ± SEM)

| Groups | Controls | Stressed |
|---|---|---|
| Vehicle | 376 ± 4 | 356 ± 12 |
| Imipramine | 350 ± 7 | 326 ± 7 |
| Vortioxetine | 348 ± 9 | 328 ± 9 |
| Nalmefene | 371 ± 9 | 355 ± 11 |
| Vortioxetine + Nalmefene | 348 ± 8 | 339 ± 10 |

Conclusions

The results of this study are consistent with our previous data showing that the CMS procedure causes a substantial decrease in the consumption of 1% sucrose solution, and that this deficit can be fully reversed by five weeks of treatment with imipramine. The onset of action of imipramine was comparable to that observed in our other CMS studies with this drug.

Nalmefene was effective in the CMS model; the compound increased sucrose drinking in stressed animals and did not affect the behaviour of control animals. The onset of action of Nalmefene was comparable to that of imipramine.

Vortioxetine was not effective in the CMS model when administered alone but when injected together with Nalmefene, the compound increased sucrose drinking in stressed animals already after first week of administration.

The time course of the sucrose consumption enhancement observed in control animals receiving Vortioxetine and Nalmefene did not parallel the effect of these drugs in stressed animals. This suggests that possible changes in thirst motivation were not responsible for the reversal of the stress-induced anhedonia caused by these drugs.

Examples 2 and 3

Other non-clinical models for characterization of an opioid antagonist with κ-activity and vortioxetine for the treatment effect on anhedonia are e.g. the Progressive Ratio responding for a natural reinforcer, and/or the Intracranial self-stimulation (ICSS) test in rodents as outlined in Examples 2-3. In each of these models, the opioid antagonist with κ-activity can be administered dissolved in an appropriate amount of an approprioate vehicle and dosed to the animals e.g. by oral, subcutaneous or intraperitoneal administration of an appropriate dose. Nalmefene can be administered e.g. in the form of nalmefene hydrochloride dissolved in an appropriate amount of an approprioate vehicle (e.g. saline or water) and dosed to the animals e.g. by oral, subcutaneous or intraperitoneal administration of an appropriate dose. Vortioxetine can be administered e.g. in the form of vortioxetine hydrobromide, vortioxetine lactate or other salts dissolved in an appropriate amount of an appropriate vehicle (e.g. saline, water or 10% 2-hydroxypropyl-β-cyclodextrin) and dosed to the animals e.g. by oral, subcutaneous or intraperitoneal administration of an appropriate dose. Additionally, the compounds can be given with the animal food in a special formulation.

Example 2

Progressive Ratio Responding for a Natural Reinforcer

The progressive-ratio schedule of reinforcement provides a measure of the motivation to consume a reward (Hodos W, Progressive ratio as a measure of reward strength, *Science* (1961); 134 (3483): 943-4; Markou et al. Animal models of craving. *Psychopharmacology* (1993) 112: 163-182). This procedure assesses the amount of effort that the animal is willing to emit to obtain a reward (e.g. sucrose, food or drug). Decreases in the amount of effort that the animal emits in a progressive-ratio schedule provides a measure of evolution, that is, lack a motivation, in addition to incentive. This method is used to access the anhedonic symptoms, since animals subjected to the effect of stressors or helpless animals do not work for the reward. Animals are initially trained on a fixed-ratio schedule 1 over 10 days. After a fixed-ratio training is completes, animals are placed on a progressive-ratio schedule to obtain the reinforcement, in which the response requirement necessary to obtain a single reinforcement increase according to the following progression: 1, 2, 4, 8, 16, 32, 64, 128, 192, 256, 384, 512, 768, 1024, 1280 to receive a reward. The number of lever presses for each reward continues to increase until the animal fails to obrain the next reward within the allowed time, 60 min. The final completed ratio is defined as a breakpoint. Decrease in the breakpoint likely reflect decreased motivation to obtain reward.

Reduced motivation is an important symptom of melancholic-type depression. Therefore, after the baseline collection test, the animals are subjected to experimental manipulation either in the form of stress (e.g. chronic mild stress, learned helplessness) or pharmacological treatment. The effect of treatment on the breaking point will be a measure of pharmacological effect of the compounds.

Example 3

Intracranial Self-stimulation (ICSS) in Rodents

ICSS is an operant behavioral paradigm in which animals learn to deliver brief electrical pulses into specific parts of their own brain hypothesized to be part of the reward pathways that mediate both natural and ICSS reward (Carlezon and Chartoff. Intracranial self-stimulation (ICSS) in rodents to study the neurobiology of motivation. *Nat Protoc.* (2007); 2 (11): 2987-95). Electrical stimulation usually consists of a 100-500 ms train of repeated pulses of sinusoidal or rectangular waveforms usually with a duration of 0.1 ms. Lowering of ICSS threshold indicates an increase in the reward value of the stimulation because less electrical stimulation is required for the subject to perceive the stimulation as rewarding. Conversely, elevations in thresholds indicate a decrease in the reward value of the self-stimulation because higher frequencies or current-intensities are required before the subject perceives the stimulation as rewarding. The ICSS procedure has several strengths and characteristics that distinguish it from other procedures used to study motivation, reward, or reinforcement.

After the baseline measurement the animals are subjected to experimental manipulation either in the form of stress or pharmacological treatment (Nielsen, Arnt and Sanchez. Intracranial self-stimulation and sucrose intake differ as hedonic measures following chronic mild stress: interstrain and interindividual differences. *Behav. Brain. Res.* (2000), 107 (1-2): 21-33).

The invention claimed is:

1. A method of treating a patient having depressive disorder with melancholic features, comprising administering a therapeutically effective amount of an opioid antagonist with κ-activity to the patient, wherein said administered opioid antagonist is nalmefene, and wherein said method further comprises administering a therapeutically effective amount of vortioxetine to the patient.

2. The method of claim 1, wherein said opioid antagonist with κ-activity is administered to the patient as a stand-alone treatment in the treatment of depressive disorder with melancholic features.

3. The method of claim 1, wherein said nalmefene is administered in a dose of between about 1 mg and about 30 mg.

4. The method of claim 1, wherein vortioxetine is administered in a dose of between about 1 mg and about 30 mg.

5. The method of claim 1, wherein said nalmefene and said vortioxetine are contained in separate unit dosage forms.

6. The method of claim 1, wherein said nalmefene and said vortioxetine are contained in the same unit dosage form.

7. The method of claim 1, wherein said method is for treating a patient having both depressive disorder with melancholic features and alcohol dependence.

8. The method of claim 1, wherein said nalmefene is administered in a dose of between about 1 mg and about 30 mg, and said vortioxetine is administered in a dose of between about 1 mg and about 30 mg.

9. The method of claim 8, wherein said opioid antagonist with κ-activity and vortioxetine are contained in separate unit dosage forms.

10. The method of claim 8, wherein said opioid antagonist with κ-activity and vortioxetine are contained in the same unit dosage forms.

11. A pharmaceutical composition comprising an opioid antagonist with κ-activity and vortioxetine together with a pharmaceutically acceptable excipient, wherein said opioid antagonist is nalmefene.

12. The pharmaceutical composition according to claim 11, wherein said composition comprises between about 1 mg and about 30 mg of nalmefene.

13. The pharmaceutical composition according to claim 11, wherein said composition comprises between about 1 mg and about 30 mg of vortioxetine.

14. The pharmaceutical composition according to claim 11, wherein said composition comprises between about 1 mg and about 30 mg of nalmefene, and between about 1 mg and about 30 mg of vortioxetine.

* * * * *